United States Patent [19]
Ko et al.

[11] Patent Number: 5,653,717
[45] Date of Patent: Aug. 5, 1997

[54] WOUND CLOSURE DEVICE

[75] Inventors: Michael Ko, Plainsboro; Malcolm Heaven, Hopewell; Douglas Hohlbein, West Trenton, all of N.J.

[73] Assignee: Urohealth Systems, Inc., Costa Mesa, Calif.

[21] Appl. No.: 519,932

[22] Filed: Aug. 28, 1995

[51] Int. Cl.$^6$ ................................................. A61B 17/04
[52] U.S. Cl. ........................ 606/144; 606/147; 606/223; 223/102
[58] Field of Search .................... 606/144, 147, 606/139, 223, 222; 223/102–104; 112/222

[56] References Cited

U.S. PATENT DOCUMENTS

| | | |
|---|---|---|
| 29,648 | 8/1860 | Drake . |
| 151,179 | 5/1874 | Waldie . |
| 818,152 | 4/1906 | Edwards . |
| 2,516,710 | 7/1950 | Mascolo . |
| 3,037,619 | 6/1962 | Stevans . |
| 4,527,564 | 7/1985 | Eguchi et al. . |
| 5,037,433 | 8/1991 | Wilk et al. ............... 606/139 |
| 5,059,207 | 10/1991 | Shah ............................ 606/223 |
| 5,152,769 | 10/1992 | Baber .......................... 606/145 |
| 5,219,358 | 6/1993 | Bendel et al. ............. 606/222 |
| 5,222,951 | 6/1993 | Abidin et al. ............. 606/1 |
| 5,304,184 | 4/1994 | Hathaway et al. ........ 606/144 |
| 5,306,280 | 4/1994 | Bergen et al. ............. 606/143 |
| 5,318,577 | 6/1994 | Li ................................. 606/147 |
| 5,320,632 | 6/1994 | Heidmueller ............... 606/144 |
| 5,336,239 | 8/1994 | Gimpelson .................. 606/223 |
| 5,350,385 | 9/1994 | Christy ........................ 606/144 |
| 5,370,646 | 12/1994 | Reese et al. ............... 606/139 |
| 5,374,275 | 12/1994 | Bradley et al. ........... 606/144 |
| 5,403,329 | 4/1995 | Hinchcliffe ................. 606/147 |
| 5,439,469 | 8/1995 | Heaven et al. ............ 606/144 |
| 5,462,561 | 10/1995 | Voda ............................ 606/144 |
| 5,468,251 | 11/1995 | Buelna ........................ 606/223 |
| 5,503,634 | 4/1996 | Christy ........................ 606/144 |

FOREIGN PATENT DOCUMENTS

| | | |
|---|---|---|
| 893054 | 5/1944 | France . |
| 628038 | 3/1936 | Germany . |
| 3639489A1 | 5/1988 | Germany . |
| 4210724C1 | 7/1993 | Germany . |
| 166102 | 11/1964 | Russian Federation . |
| 1309971 | 5/1987 | Russian Federation . |
| 1319836 | 6/1987 | Russian Federation . |
| 1572613 | 6/1990 | Russian Federation . |
| 1396 | 6/1910 | United Kingdom . |

OTHER PUBLICATIONS

REMA–Medizintechnik GmBH, "Innovation Through Progress," 8 pages.
Product Brochure—"The Endo–Judge from Synergistic™," 2 pages.

*Primary Examiner*—Michael Buiz
*Assistant Examiner*—Patrick W. Rasche
*Attorney, Agent, or Firm*—Burns, Doane, Swecker & Mathis, L.L.P.

[57] ABSTRACT

A wound closure device which maintains pneumoperitoneum while allowing a surgeon to capture an mount of tissue which is substantially wider than the diameter of a trocar cannula through which the device is inserted. The wound closure device includes, an elongated guide member, a hook shaped needle and a retracting mechanism for moving the needle from an open position to a closed position. In the closed position, the tip of the needle is positioned within the guide member so that the needle can be easily inserted into a body. In the open position, the needle tip is positioned outside of the guide member at a distance from the guide member which is greater than the diameter of the guide member. The device is inserted into a body through a wound in the closed position, the needle is deployed within the body by a handle and then the needle is drawn through the tissue to suture the wound

19 Claims, 4 Drawing Sheets

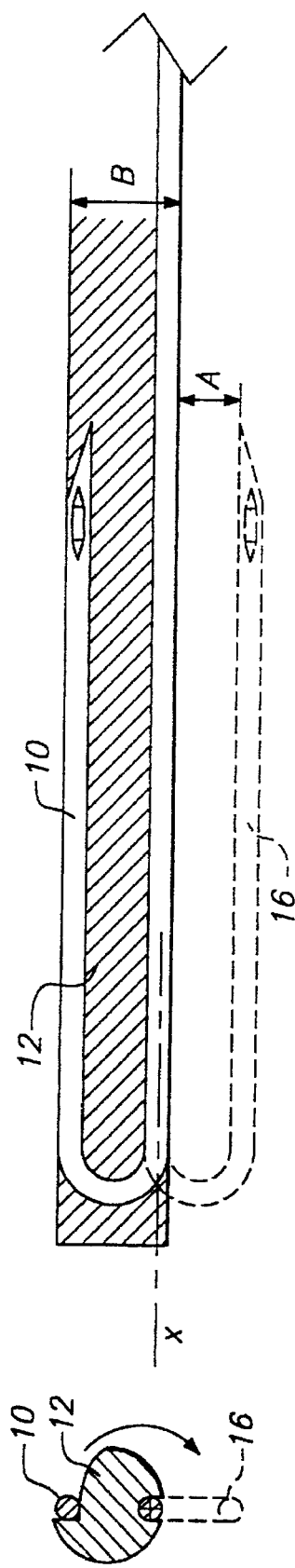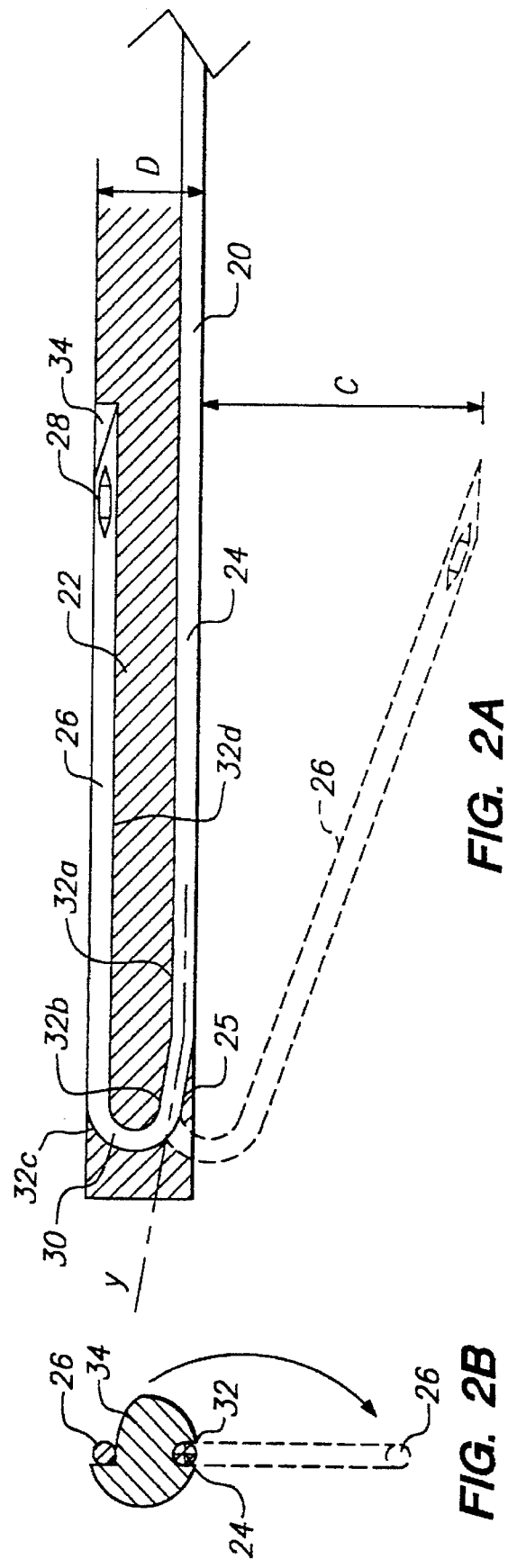
FIG. 1A PRIOR ART
FIG. 1B PRIOR ART
FIG. 2A
FIG. 2B

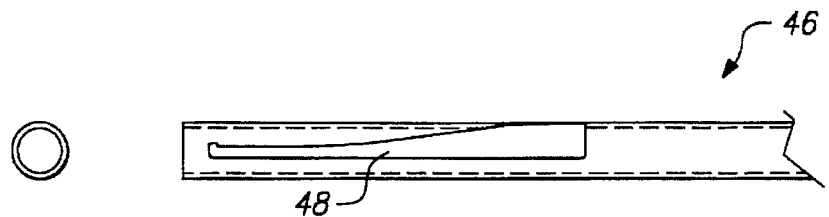
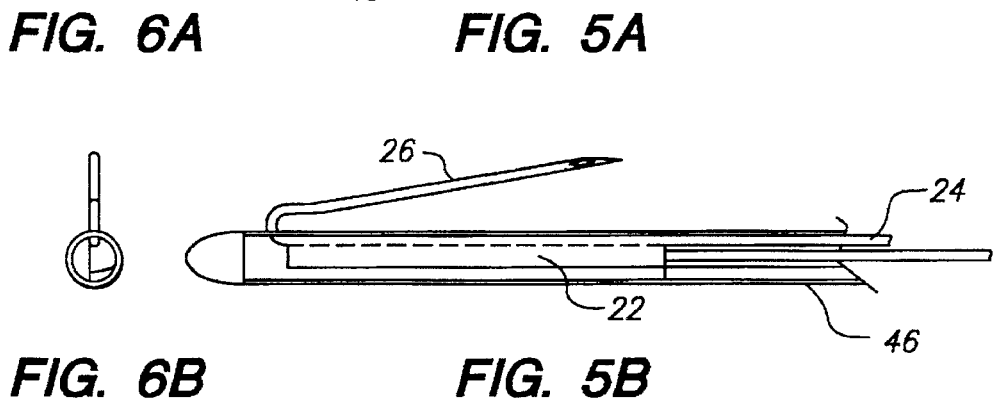
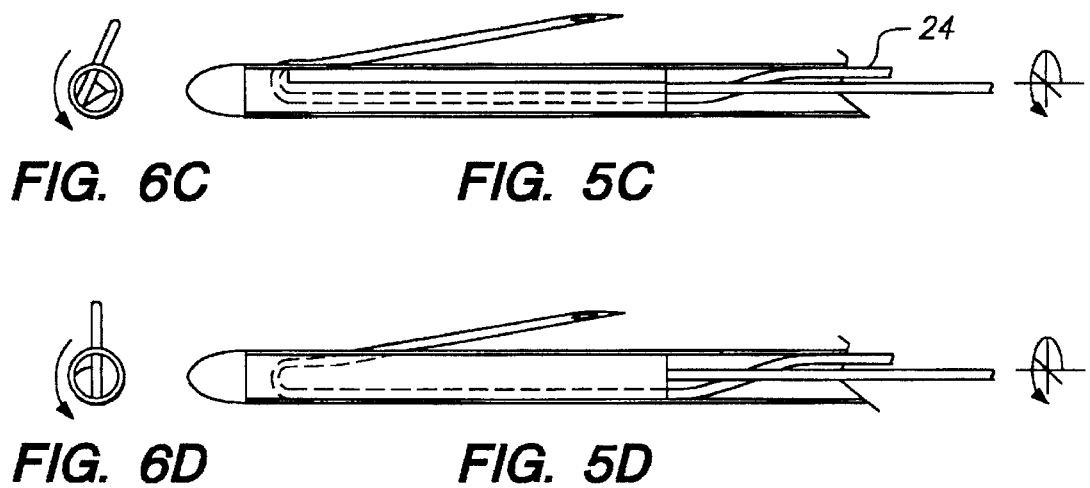
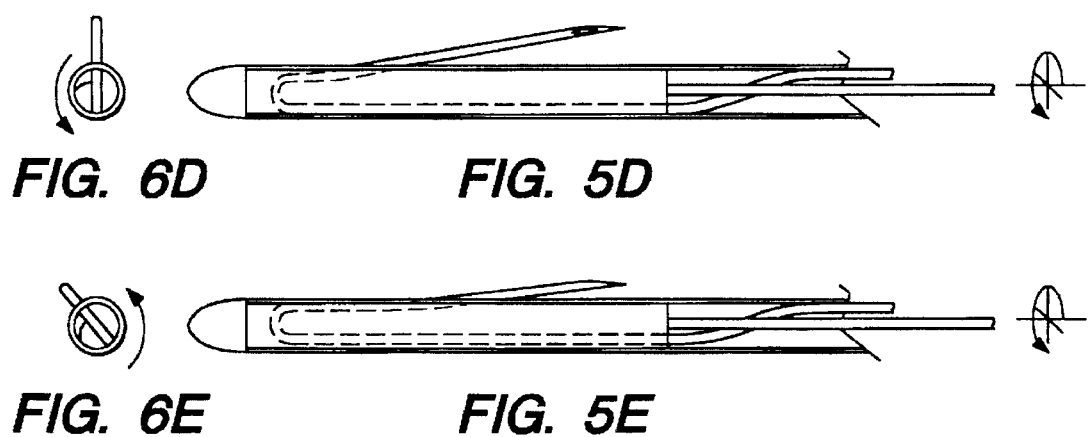
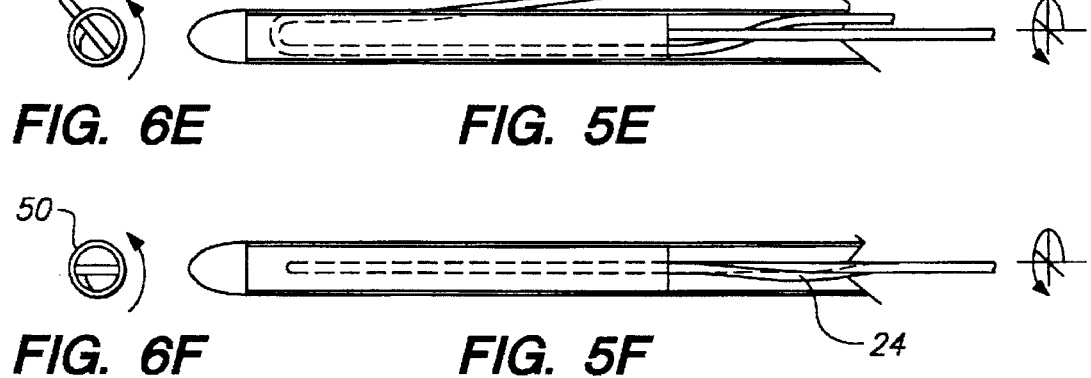
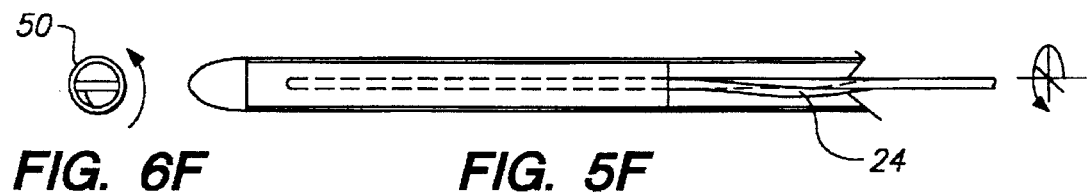
FIG. 6A    FIG. 5A
FIG. 6B    FIG. 5B
FIG. 6C    FIG. 5C
FIG. 6D    FIG. 5D
FIG. 6E    FIG. 5E
FIG. 6F    FIG. 5F

WOUND CLOSURE DEVICE

BACKGROUND OF THE INVENTION

1. Field of the Invention

The invention relates to a device to enable the closure of puncture wounds made by trocars during laparoscopic and other minimally invasive surgical procedures. More specifically, the device relates to a hook shaped device which brings together the edges of the deep tissue layers on opposing sides of a puncture wound by passing a suture through the deep tissue structures, under the skin tissue layer on opposite sides of the wound.

2. Description of the Related Art

It is known to suture puncture wounds such as those formed by trocars during laparoscopic and minimally invasive surgical procedures with a J-shaped needle such as the needle disclosed in U.S. Pat. No. 5,336,239. A J-shaped needle may be used to pass a suture through the deep tissue layers on opposing sides of a puncture wound such as the peritoneal membrane and deep abdominal fascia punctured during laparoscopic abdominal surgery. The point of the J-shaped needle may be covered as the needle is inserted into the puncture wound. The needle is then exposed from the cover and drawn outward through the subcutaneous tissue layers and finally through the skin on a side of the wound. The surgeon then threads a length of suture through the eye of the needle and draws the needle back through the skin and tissue into the body. The needle is passed out of the body through the tissue at another location on an opposite side of the wound completing the suture. This process is repeated as necessary to close the wound.

One of the disadvantages of the devices of the prior art such as the one disclosed in U.S. Pat. No. 5,336,239, is that, in order to be insertable through a trocar cannula, the needle profile has to be equal to or less than the internal diameter of the trocar cannula. For example, in currently available devices, if the internal diameter of the trocar cannula is 10 mm, then the width of the J-shaped needle measured from the widest point on the outside of the short leg of the "J", to the outside of the long leg of the "J" must be equal to or less than 10 mm. With this restriction the amount of "bite" that the prior art device can achieve (i.e., the amount of tissue it can capture for suturing) is limited to the maximum gap between the two legs of the "J" shaped needle. This is an unwanted limitation on the ability to secure the tissue under certain circumstances.

Examples of J-shaped needles are disclosed in commonly-owned U.S. patent application Ser. Nos. 08/134,561 and 08/145,855 now U.S. Pat. Nos. 5,468,251 and 5,439,469 respectively. One embodiment of such needles is shown in FIGS. 1A and 1B. The needle 10 is housed in a cylindrical guide member 12 during insertion of the needle into a patient. After insertion, the needle 10 is rotated 180 degrees with respect to the guide member 12 about an axis x of the longer leg of the needle. As shown in phantom lines in FIGS. 1A and 1B, the short leg 16 of J-shaped needle 10 when rotated 180 degrees is positioned at a distance (a) from the guide member 12. The distance (a) is less than the diameter (b) of the guide member 12. As a result, the amount of tissue which can be captured between the short leg 16 and the housing 12 is rather limited.

Other types of needle arrangements are disclosed in WO93/21831, WO92/12674, EP 589409 A1, EP 568098 A2 and U.S. Pat. Nos. 5,222,508, 5,281,237, 5,350,385 and 5,320,632.

SUMMARY OF THE INVENTION

The invention provides a wound closure device comprised of an elongated guide member and needle having a needle tip positioned within the guide member in a closed position and positioned outside the guide member in an open position, the guide member and the needle tip being spaced apart by a distance greater than the external diameter of the guide member when the needle is in the open position. The device further includes a retraction mechanism for moving the needle from the open position to the closed position.

The needle preferably comprises a hook shaped needle having a first leg connected to a second leg by a distal end of the needle, the second leg including a needle tip and when the needle tip is in the open position the second leg extends at an angle with respect to the first leg such that a distance between the first leg and the second leg decreases at locations along the second leg away from the tip.

BRIEF DESCRIPTION OF THE DRAWINGS

The invention is described with reference to the accompanying drawings in which like elements bear like reference numerals, and wherein:

FIG. 1A is a sectional side view of a comparative wound closure device having a limited "bite";

FIG. 1B is a sectional end view of the device of FIG. 1A;

FIG. 2A is a sectional side view of a wound closure device according to a first embodiment of the present invention;

FIG. 2B is a sectional end view of the device of FIG. 2A;

FIG. 5A is a side view of a sleeve for use with a wound closure device according to a third embodiment of the invention;

FIGS. 5B–5F are side views, partly in section, of the operation of a third embodiment of the invention;

FIGS. 6A–6F are end views corresponding to FIGS. 5A–5F;

DETAILED DESCRIPTION OF THE PREFERRED EMBODIMENTS

Figures 3A, 4A:
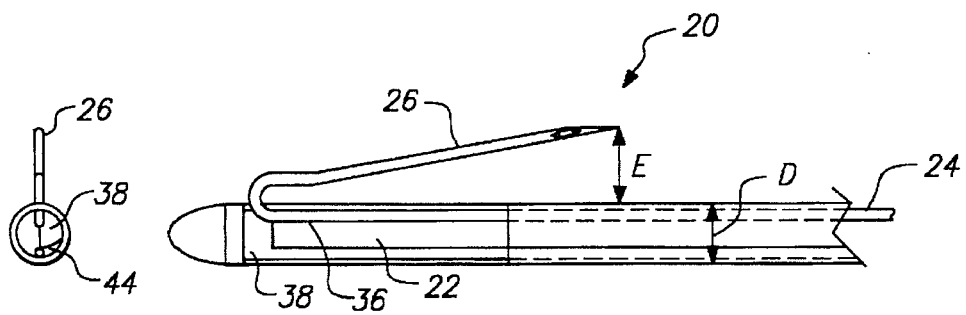
FIGS. 3A–3E are side views of the operation of a wound closure device according to a second embodiment of the invention.
FIGS. 4A–4E are end views corresponding to FIGS. 3A–3E.

The invention provides a wound closure device which can maintain pneumoperitoneum during a laparoscopic surgical operation and allow the surgeon to capture an mount of tissue which is substantially wider than the diameter of the trocar cannula through which the needle is inserted. As shown in FIG. 2A, the suturing device includes a hook shaped needle 20 and a guide member 22. The hook shaped needle 20 includes a long leg 24 which extends to a handle (not shown) and a short leg 26 having an eye 28 for receiving a suture near a sharpened tip of the needle. In the closed position, the needle 20 is fully within guide member 22. The hook shaped needle 20 is designed such that short leg 26 of the needle, in its deployed (open) condition, is tilted or angled, with respect to the long leg 24 of the needle. Therefore, the distance C between the tip of the needle and an adjacent wall of the guide member 22 is greater than the external dimension of guide member 22 and consequently greater than an inner diameter of a trocar cannula (not shown) through which the entire device can be inserted into a patient. In the deployed condition, shown in phantom lines in FIGS. 2A and 2B, a distal curve or bend 30 of the needle 20 is partially exposed outside the guide member 22, the bend 30 having a non-traumatic shape and providing sufficient width between the needle tip and the guide member. Due to the wedge-shaped opening between short leg 26 and guide member 22, tissue captured with the needle during suturing is not severed or excessively compressed within the base of the needle as the device is drawn through the tissue.

The wound closure device can include various retraction mechanisms for deploying the needle to the open position and retracting the needle to the closed position. In the closed position, a trocar cannula can be slid over the device and removed, if desired. If the trocar cannula is removed, a portion of the guide member 22 above the tip of the needle will maintain pneumoperitoneum during the suturing operation.

According to the embodiment of the invention shown in FIGS. 2A and 2B, the needle 20 has the shape shown in phantom in the open, unconstrained stated. As shown in FIG. 2A, the long leg 24 of the hook shaped needle 20 is located in a slot 32 extending along the outer wall of the guide member 22 which restrains the needle longitudinally, but allows rotation of the long leg 24 of the needle with respect to its longitudinal axis. The slot 32 includes a first portion 32a parallel to long leg 24, a second portion 32b receiving portion 25 of the needle and extending at an obtuse angle to the first portion, a third portion 32c perpendicular to the first portion 32a and receiving distal end 30 of the needle and a fourth portion 32d parallel to first portion 32a and receiving short leg 26. The second portion 32b extends in direction y at an acute angle (e.g., ≦30°) with respect to the central axis of the guide member 22.

Upon rotation of long leg 24, the second portion 32b and first portion 32a cause the portion 25 to elastically bend with respect to long leg 24 and thus orient the short leg 26 parallel to the long leg 24 when the needle 20 is rotated into the closed position. Conversely, to open the needle, the needle 20 is rotated about the axis of long leg 24 to deploy short leg 26 to the open position whereupon the force constraining elastically deformed portion 25 is gradually released until short leg 26 is in the position shown in phantom in FIG. 2A. To accommodate short leg 26 as it rotates into and out of guide member 22, portion 32d of slot 32 includes circumferentially extending recess 34.

In order to facilitate the flexing of the short leg 26 of the needle, the profile of portion 25 could be modified to accommodate bending, for example, by reducing the diameter of the needle. Alternatively, portion 25 could comprise a section of more resilient material than that of long leg 24 and/or short leg 26. Whether or not long leg 24, bend 25, distal end 30 and short leg 26 are of the same material (e.g., stainless steel) or not, when long leg 24 is rotated by a handle (not shown), the point of the needle is rotated in a non-circular path deploying the tip of the needle well outside of the outer surface D of the guide member 22. Preferably, the distance C between the tip of the needle in the open position and the outer surface of the guide member 22 is at least twice the maximum transverse dimension D of the guide member 22. Upon 180° rotation of the long leg 24, the short leg 26 of the needle is flexed inwardly toward the guide member and rotates along recess 34 into portion 32d of slot 32, such that the needle tip is again constrained within the guide member.

A second embodiment of the invention is shown in FIGS. 3A–3E and 4A–4E. In this embodiment, the long leg 24 of the hook shaped needle 20 is positioned along the inside wall of the guide member 22 within a slot 36 in the guide member which restrains the needle longitudinally but allows axial rotation of the needle about the long leg. In the fully deployed condition, shown in FIGS. 3A and 4A, the tip of the needle is rotated 180 degrees outside of the guide member 22 such that the tip is positioned at a distance E from the outer surface of the guide member 22, distance E exceeding the dimension D of the guide member.

Figures 3B, 4B:
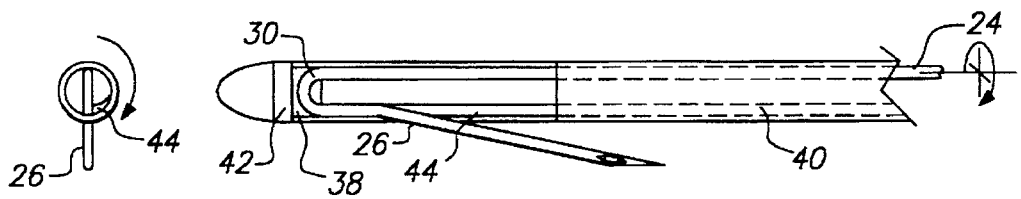
Figures 3C, 4C:
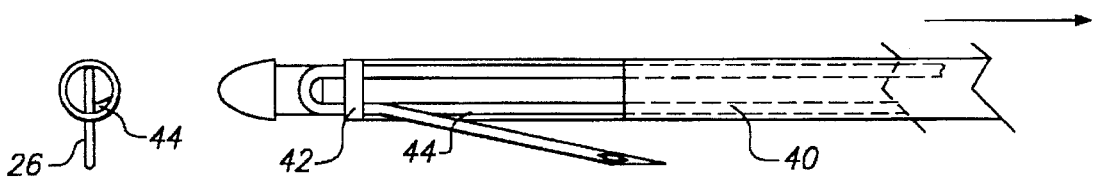
Figures 3D, 4D:
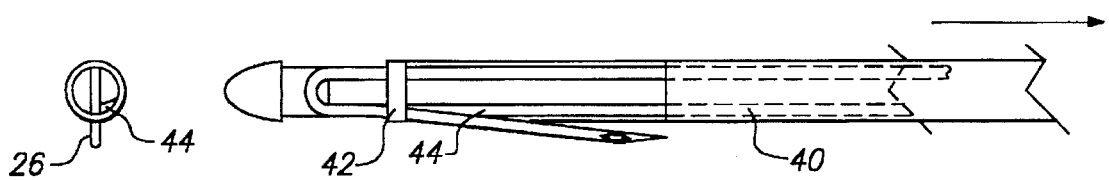
Figures 3E, 4E:
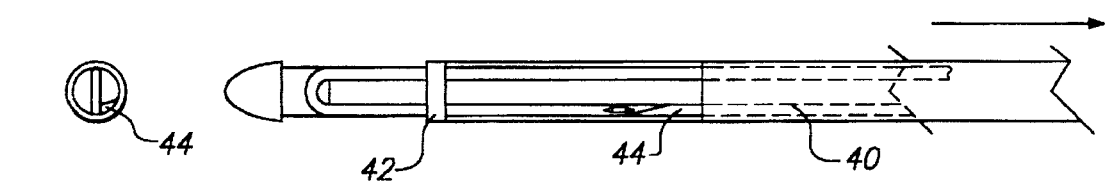

To close the device, the hook shaped needle 20 is first axially rotated 180 degrees with respect to the body of the device as shown in FIGS. 3B and 4B, causing the curved distal end 30 of the hook to rotate into a recess 38 provided across the diameter of the distal end of the guide member 22. This effectively closes the needle an amount equal to the diameter of the guide member 22, leaving only the angled short leg 26 of the needle exposed beyond the outer surface of the guide member. A retracting mechanism 40 mounted on the outside of the guide member 22 is movable longitudinally and causes an outer, thin-walled ring 42 of the retracting mechanism to slide over the outside diameter of the guide member, over the distal base of the needle, until it engages the exposed, angled short leg 26 of the needle as shown in FIGS. 3C and 4C. On continued axial sliding of the outer retracting mechanism 40 up the guide member 22, the edge of the ring 42, acting as a ramp, elastically deforms the short leg 26 of the needle to flex and bend under the edge of ring 42 as shown in FIGS. 3D and 4D, until the short leg of the needle is elastically deformed into a receiving groove 44 in the side of the guide member 22, as shown in FIGS. 3E and 4E, completely closing the device and allowing the device to be inserted or withdrawn from a surgical site while maintaining peritoneum. If desired, ring 42 can be incorporated in a tubular sleeve having cut-outs for allowing deployment and retraction of short leg 26.

In order to open the needle once the device has been inserted into the body of a patient, the steps shown in FIGS. 3A–3E and 4A–4E are conducted in reverse order. That is, the retracting mechanism 40 is slid distally along the guide member 22 to release the tip of the needle from the ring 42 such that the tip is angled outwardly away from long leg 24. Then the long leg 24 of the needle is rotated 180 degrees with respect to the guide member 22 so that the short leg 26 and the distal end 30 of the needle are entirely outside of the guide member 22.

According to a third embodiment of the invention shown in FIGS. 5A–5F and 6A–6F, the long leg 24 of the hook shaped needle is disposed inside guide member 22 which is positioned inside a sleeve 46. The sleeve 46, as shown in FIGS. 5A and 6A, includes a tubular member configured to fit over the guide member 22. The sleeve 46 has a longitudinal tapered slot 48 through which the short leg 26 of the needle extends. One edge of the longitudinal slot 48 has an arc shape such that the width of the slot increases along the length of the slot, from the distal end to the proximal end of the slot.

In the deployed condition, as shown in FIGS. 5B and 6B, the needle is restrained at its proximal end such that the long leg 24 lies along the inside wall of the sleeve 46, and the short leg 26 of the needle extends out of the slot 48 in the side of the sleeve 46, beyond the outer surface of the device. To close the device, a rotary mechanism (not shown) rotates the guide member 22 with respect to the sleeve 46. The rotation of the guide member 22 moves the long leg 24 laterally away from the slot 48 and draws distal end 30 into the guide member 22, as shown in FIGS. 5C, 5D, 6C and 6D. For instance, this lateral movement can be accomplished by twisting long leg 24 of the needle into a helical shape across the internal diameter of the stationary sleeve 46, as shown in FIGS. 5C and 5D. Such movement partially closes the needle by an amount equal to the internal diameter of the sleeve 46, leaving only the short leg 26 of the needle exposed outside of the slot 48 in the sleeve 46. To complete the closure of the device, the guide member 22 is rotated with respect to sleeve 46 such that the arc shaped side of the slot 48 engages the exposed short leg 26 of the needle, where it acts as a ramp and forces the short leg of the needle to flex under the edge of the arc as shown in FIGS. 5E and 6E. The rotation of the guide member 22 continues until the short leg of the needle is elastically deformed into a receiving groove 50 in the side of the guide member 22, within the diameter of the sleeve 46, completely closing the device.

Alternatively, sleeve 46 can be used with the device shown in FIGS. 5A–F. That is, bend 30 can be drawn into the guide member in the manner shown in FIGS. 3A–F by moving long leg 24 along a circumferential path away from slot 48. To complete closure of the needle, sleeve 46 can be used in place of ring 42 to flex short leg 26 into the guide member by engaging short leg 26 with an edge of slot 48. Thus, bend 30 would be moved into and out of the guide member by rotating guide member 22 with respect to sleeve 46 and upon further rotation of sleeve 46 the short leg 26 would be engaged with slot 48.

Figure 7A:
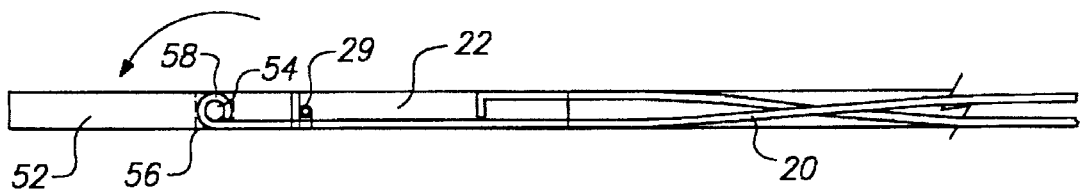
FIGS. 7A–7C are side views of the operation of a handle useable with the embodiments of FIGS. 5A–5F and 6A–6F.
Figure 7B:
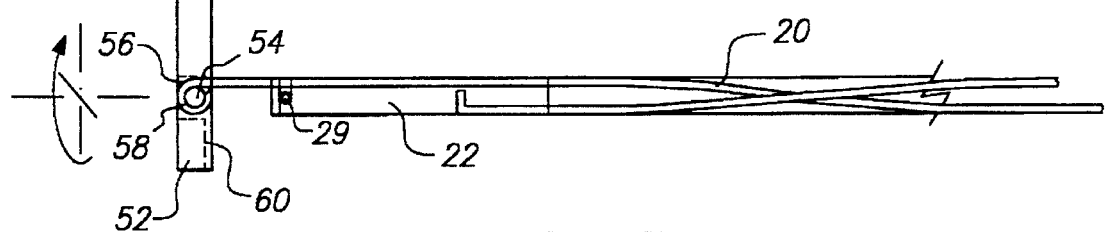
Figure 7C:
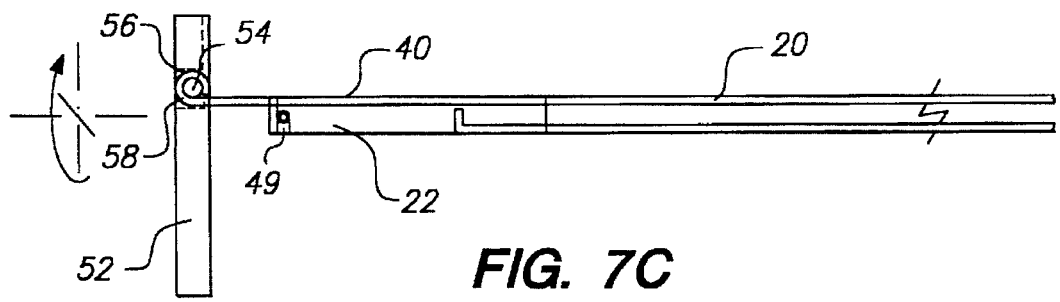

In the foregoing embodiments, a deployable handle may be attached to the proximal end of the long leg 24 of the needle to provide a secure grasp of the device in the hands of the surgeon and to provide a visual and tactile indication of the orientation of the needle during use. An example of such a handle 52 is shown in FIGS. 7A–7C. The handle 52 is especially useful for identifying the orientation and position of the deployed needle point when it is hidden from view within a body cavity.

The handle 52 is preferably formed as a cylindrical rod whose diameter is less than or equal to the external diameter of the device whereby the device and the handle 52 can pass freely through a trocar cannula in the case where a trocar cannula is used to introduce the guide member 22 into an operative site and the trocar cannula is subsequently removed. The handle 52 may be attached to the needle 20 via a pin 54 which is pressed through a slot 56 in the handle 52. A loop 58 formed at the end of the needle 20 is inserted in the slot 56 and the pin 54 is inserted through the loop. The pin 54 acts as a pivot about which the handle 52 may be rotated with respect to the device to form a "T". The position of the pivot pin 54 and the slot 56 through the handle, are preferably placed off-center such that the two portions of the "T" handle are asymmetrical and provide visual and tactile information as to the orientation of the deployed needle, e.g., the portion of the handle extending further from the pivot indicating the direction of the needle tip. The handle 52 also includes a slot 60 which accommodates the proximal end of the long leg 24 of the needle when the handle is in the closed position.

FIGS. 7A–7C show the operation of the handle 52. In FIG. 7A, the handle is in the closed position parallel to the axis of the guide member to allow removal of a trocar cannula over the device. After insertion of the device into the body, the handle can be pivoted 90 degrees so as to be perpendicular to the axis of guide member 22, as shown in FIG. 7B. Thereafter, the handle is rotated 180 degrees to deploy the needle as shown in FIG. 7C. Rotation of needle 20 with respect to the guide member 22 and sleeve 40 can be limited in any suitable manner, if desired. For instance, a stop member 29 (e.g., pin) attached to guide member 22 can be used to limit longitudinal movement and rotation of the guide member with respect to sleeve 40. As an example, stop member 29 can extend through a circumferentially extending slot 49 in sleeve 40 to limit rotation.

Figure 8:
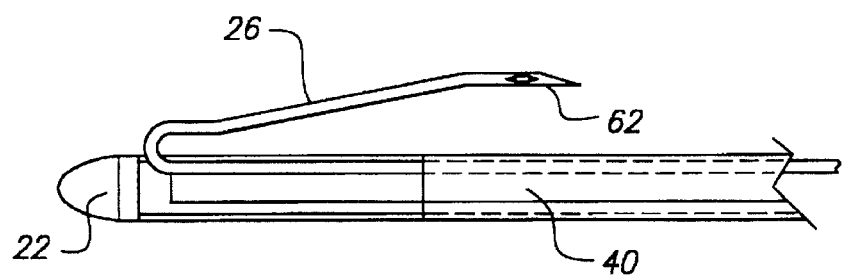
FIG. 8 is a side view of a wound closure device according to a fourth embodiment of the invention.

In all of the embodiments discussed above, a variation of the hook shaped needle can be employed, in which the tip of the angled hook of the short leg 26 curves back in towards the body of the device, whilst still maintaining the desired bite width which is greater than the diameter of the closed device. The "recurved" tip 62 is shown in FIG. 8 in which the recurved tip 62 is parallel to the body of the device. This "recurved" tip may aid the surgeon in exiting the tissue at a desired angle during suture placement.

In a preferred embodiment of the invention, a recess (not shown) is incorporated in the guide member of the device, in the region in which the tip and eye of the needle are sheathed when the device is in a completely closed position. This recess extends on both sides of the groove which receives the short leg of the needle. The recess provides clearance for a loop of suture material which is threaded through the eye of the needle and remains attached to the needle in the closed position. This allows the surgeon the option of pre-threading the needle with suture prior to insertion of the device into the patient.

In all embodiments, the device is designed to be completely exchangeable through the bore of the trocar cannula in either direction and designed such that operative pneumo (i.e. pneumoperitoneum or pneumothorax or properitoneal pneumo) is maintained during use. These features result in maximum safety to the patient and allow the surgeon the choice of using the device with the trocar cannula in place or removed.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A wound closure device comprising:
    an elongated guide member extending in a longitudinal direction and having a maximum width in a lateral direction allowing the guide member to pass through a trocar cannula, the guide member maintaining pneumoperitoneum during a laparoscopic suturing operation with the wound closure device;
    a needle supported by the guide member so as to be movable laterally towards and away from an outer surface of the guide member, the needle including a needle tip, the needle tip being movable in the lateral direction from a closed position within the guide member to an open position outside the guide member, a distance in the lateral direction between the outer surface of the guide member and the needle tip at the open position being greater than the maximum width of the guide member;
    a retraction mechanism engageable with the needle so as to elastically deform the needle tip into the closed position, the retraction mechanism being movable with respect to the guide member and including a sleeve surrounding the guide member.

2. The wound closure device of claim 1, wherein the needle is J-shaped, the needle having a straight long leg, a straight short leg and a distal bend connecting the long leg to the short leg, the short leg having the needle tip at one end thereof, the needle being elastically deformed such that the short leg is parallel to the long leg when the needle is in the closed position and the short leg forming an acute angle with the long leg when the needle is in the open position.

3. The wound closure device of claim 1, wherein the retraction mechanism includes a handle which rotates the needle with respect to the guide member to move the needle tip from the closed position to the open position.

4. The wound closure device of claim 3, wherein the guide member includes a slot accommodating a portion of the needle, the slot including a first portion extending along a side of the guide member and a second portion extending toward a center axis of the guide member, the first portion forming an obtuse angle with the second portion.

5. The wound closure device of claim 1, wherein the retraction mechanism includes a retraction member movably mounted on the guide member.

6. The wound closure device of claim 5, wherein the retraction member includes a ring which slides along the guide member and engages a portion of the needle to move the needle to the closed position.

7. The wound closure device of claim 1, wherein the sleeve includes a tapered slot, the tapered slot having an edge engageable with the needle to move the needle to the closed position.

8. The wound closure device of claim 7, wherein the sleeve is rotatable with respect to the guide member, the edge of the slot engaging the needle by rotating the sleeve.

9. The wound closure device of claim 1, further comprising a handle providing a visual indication of the orientation of the needle tip.

10. The wound closure device of claim 1, wherein the retraction mechanism rotates the needle and elastically deforms a portion of the needle connected to the needle tip as the needle tip moves to the closed position.

11. The wound closure device of claim 1, wherein the guide member includes a slot extending in the longitudinal direction along one side thereof and a recess along an opposite side thereof, the needle being J-shaped and including a long leg and a short leg, the long leg being in the slot and the short leg being located in the recess when the needle is in the closed position.

12. The wound closure device of claim 1, wherein the guide member is cylindrical and has a substantially uniform diameter, the retraction mechanism comprising the sleeve surrounding the guide member.

13. The wound closure device of claim 12, wherein the sleeve engages a portion of the needle and elastically deforms the portion while moving the needle to the closed position.

14. The wound closure device of claim 1, wherein the retraction mechanism includes a rotatable sleeve which is mounted on and rotatable about the guide member, the rotatable sleeve including a circumferentially extending guide slot and the guide member including a stop member located in the guide slot for limiting rotation of the sleeve relative to the guide member.

15. The wound closure device of claim 1, wherein the needle is J-shaped with a long leg, short leg and distal bend connecting the long leg to the short leg, the long leg being parallel to the short leg when the needle is in the closed position and the long leg being at an acute angle to the short leg when the needle is in the open position.

16. The wound closure device of claim 1, wherein the needle includes a short leg having the needle tip at a free end thereof, a long leg and a distal portion connecting the long leg to the short leg, the distal portion being movable laterally in a plane parallel to the longitudinal direction into and out of a slot in the guide member during partial movement of the needle tip from the closed position to the open position.

17. The wound closure device of claim 1, wherein the needle includes a short leg having the needle tip at a free end thereof, a long leg and a distal portion connecting the long leg to the short leg, the distal portion being movable laterally in a circumferential path into and out of a slot in the guide member during movement of the needle tip to the open position.

18. A wound closure device comprising:

an elongated guide member extending in a longitudinal direction and having a maximum width in a lateral direction allowing the guide member to pass through a trocar cannula;

a needle supported by the guide member so as to be movable laterally towards and away from an outer surface of the guide member, the needle including a needle tip, the needle tip being movable in the lateral direction from a closed position within the guide member to an open position outside the guide member, a distance in the lateral direction between the outer surface of the guide member and the needle tip at the open position being greater than the maximum width of the guide member; and a retraction mechanism engageable with the needle so as to move the needle tip into the closed position; and a handle providing a visual indication of the orientation of the needle tip the handle being pivotably attached to the needle such that the handle can be positioned with an axis of the handle perpendicular to a longitudinal axis of the guide member or positioned such that the axis of the handle is parallel to the longitudinal axis of the guide member.

19. A wound closure device comprising:

an elongated guide member extending in a longitudinal direction and having a maximum width in a lateral direction allowing the guide member to pass through a trocar cannula;

a needle supported by the guide member so as to be movable laterally towards and away from an outer surface of the guide member, the needle including a needle tip, the needle tip being movable in the lateral direction from a closed position within the guide member to an open position outside the guide member, a distance in the lateral direction between the outer surface of the guide member and the needle tip at the open position being greater than the maximum width of the guide member; and a retraction mechanism engageable with the needle so as to move the needle tip into the closed position, the guide member being cylindrical and including a longitudinally extending slot for accommodating a portion of the needle, the slot including a first straight portion extending along a side of the guide member and a second straight portion extending at an acute angle to a longitudinal axis of the guide member, the portion of the needle being rotatably mounted in the first and second portions of the slot so as to be elastically deformed when the needle tip is in the closed position.

* * * * *